United States Patent [19]

Zaiger et al.

[11] Patent Number: Plant 5,832

[45] Date of Patent: Dec. 16, 1986

[54] PEACH TREE

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 698,526

[22] Filed: Feb. 4, 1985

[51] Int. Cl.[4] ..... A01H 5/03

[52] U.S. Cl. ..... Plt./43

[58] Field of Search ..... Plt./43

*Primary Examiner*—Robert E. Bagwill

[57] ABSTRACT

Our new development relates to a distinct variety of peach tree. Its novelty consists of the following unique combination of features which are outstanding in a new variety:

1. The large size of the fruit.
2. The extreme firmness of the fruit and its good shipping and storage qualities.
3. Heavy and regular production.
4. Smooth round fruit contributing to ease of handling.
5. A high degree of attractive red skin color.
6. Excellent eating quality

1 Drawing Figure

ORIGIN OF THE VARIETY

The present variety of peach tree was originated by us at the experimental farm located at Modesto, Calif., from a cross between O'Henry Peach (U.S. Plant Pat. No. 2,964) and June Lady Peach (U.S. Plant Pat. No. 3,022). A large group of seedlings from this cross were maintained and grown under close observation by us and the present variety which evidenced distinctive desireable characteristics was selected for propagation and commercialization.

ASEXUAL REPRODUCTION OF THE VARIETY

Asexual propagation of our new variety by budding was performed at the experimental orchard located at Modesto, Calif. and shows that all characteristics come true to form and are established and transmitted through succeeding propagations.

SUMMARY OF THE VARIETY

Our new and distinct variety of peach tree is of large size, vigorous, upright growth and a productive and regular bearer of large, firm, yellow flesh, freestone fruit. The fruit maturing approximately 10 days earlier than O'Henry Peach (U.S. Plant Pat. No. 2,964) and having a high degree of attractive red skin color.

DESCRIPTION OF THE PHOTOGRAPHS

The accompanying photographs show reproductions in color of the foliage and fruit of our new variety with the upper and lower surface of the leaves being illustrated and a exterior and sectional view of the fruit being shown with the stone in place. The photographs were taken shortly after being picked at maturity (shipping ripe) and the colors are as nearly true as is reasonably possible in a color representation of this type.

DESCRIPTION OF THE VARIETY

The following is a botanical description of the fruit and foliage of our new peach variety, as based on observations of specimens grown at Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Productivity.*—Productive.
- *Bearer.*—Regular.

Trunk:
- *Size.*—Medium to large.
- *Texture.*—Medium shaggy.
- *Color.*—Brownish gray.

Branches:
- *Size.*—Medium.
- *Texture.*—Medium rough.
- *Lenticels.*—Medium number Medium size.
- *Color.*—Brown to grayish brown.

Leaves:
- *Size.*—Large. Average length — $6\frac{3}{4}''$. Average width — $1\frac{7}{8}''$.
- *Form.*—Lanceolate. Acutely pointed.
- *Texture.*—Smooth.
- *Margin.*—Crenate.
- *Petiole.*—Size — medium. Average length — $\frac{1}{2}''$. Average width — 1/16". Longitudinally grooved.
- *Glands.*—Number 2 to 6. Average number 3. Reniform. Located on lower part of leaf blade and upper part of petiole.
- *Color.*—Upper surface — deep green (28-E-5 to 28-F-6). Lower surface — grayish green (28-D-5 to 28-D-7).

Flower buds:
- *Size.*—Medium to large.
- *Form.*—Plump.
- *Pubescence.*—Pubescent.

Flowers:
- *Size.*—Medium — non-showy.
- *Blooming period.*—Mar. 2, 1982 to Mar. 8, 1982. Varies slightly with climatic conditions.
- *Pollen.*—Present.
- *Color.*—Pink.

Fruit:
- *Maturity when described.*—Firm ripe.
- *Date of first picking.*—July 28, 1982.
- *Date of last picking.*—Aug. 4, 1982.

*Size.*—Large. Average diameter axially — $2\frac{7}{8}''$ to 3 3/16". Average transversely in suture plane $2\frac{3}{4}''$ to 3".

*Form.*—Nearly globose — slightly flattened at stem end.

*Suture.*—Distinct but shallow — extends from apex to base.

*Ventral surface.*—Usually rounded, varies from equal to slightly unequal.

*Cavity.*—Rounded to slightly elongated in suture plane. Average depth — $\frac{1}{2}''$. Average breadth — $\frac{5}{8}''$.

*Base.*—Rounded to slightly retuse.

*Apex.*—Rounded — pistol point slightly depressed.

Skin:

*Thickness.*—Thick to medium.

*Texture.*—Tough — tenacious to flesh.

*Tendency to crack.*—None.

*Down.*—Moderate — medium length.

*Color.*—Bright yellow ground color (4-A-8 to 5-A-8) overspread with red (8-A-8 to 9-B-8).

Flesh:

*Color.*—Dark yellow (4-A-8) to golden yellow (5-B-7). Pit cavity red (9-A-7) extending into flesh in some areas.

*Texture.*—Firm.

*Fibers.*—Few — tender.

*Juice.*—Moderate.

*Amygdalin.*—Undetected.

*Ripens.*—Uniform.

*Flavor.*—Mild.

*Aroma.*—Distinct.

*Eating quality.*—Excellent.

Stone:

*Type.*—Freestone.

*Size.*—Large. Average length — 17/16". Average width — 1". Average thickness — $\frac{5}{8}''$.

*Form.*—Ovid.

*Base.*—Usually straight.

*Apex.*—Acuminate.

*Sides.*—Usually unequal — some equal.

*Surface.*—Furrowed toward apex and pitted toward base.

*Ridges.*—Rounded.

*Tendency to split.*—Very slight.

*Color.*—Brown (8-C-4 to 8-D-4).

Use:

*Market.*—Local and long distance. Dessert.

Storage quality: Very good.

Shipping quality: Very good.

The new variety of peach tree herein described can vary in slight detail due to climatic, soil conditions and cultural practices under which the variety may be grown, the present description is that of the variety grown at Modesto, Calif.

We claim:

1. A new and distinct variety of peach tree which is of large size, vigorous, upright growth, and a productive and regular bearer of large size, yellow flesh, freestone fruit, maturing approximately 10 days before O'Henry Peach (U.S. Plant Pat. No. 2,964); the fruit is further characterized by its high degree of red skin color, its excellent eating quality and a high degree of firmness when mature with very good shipping and storage quality.

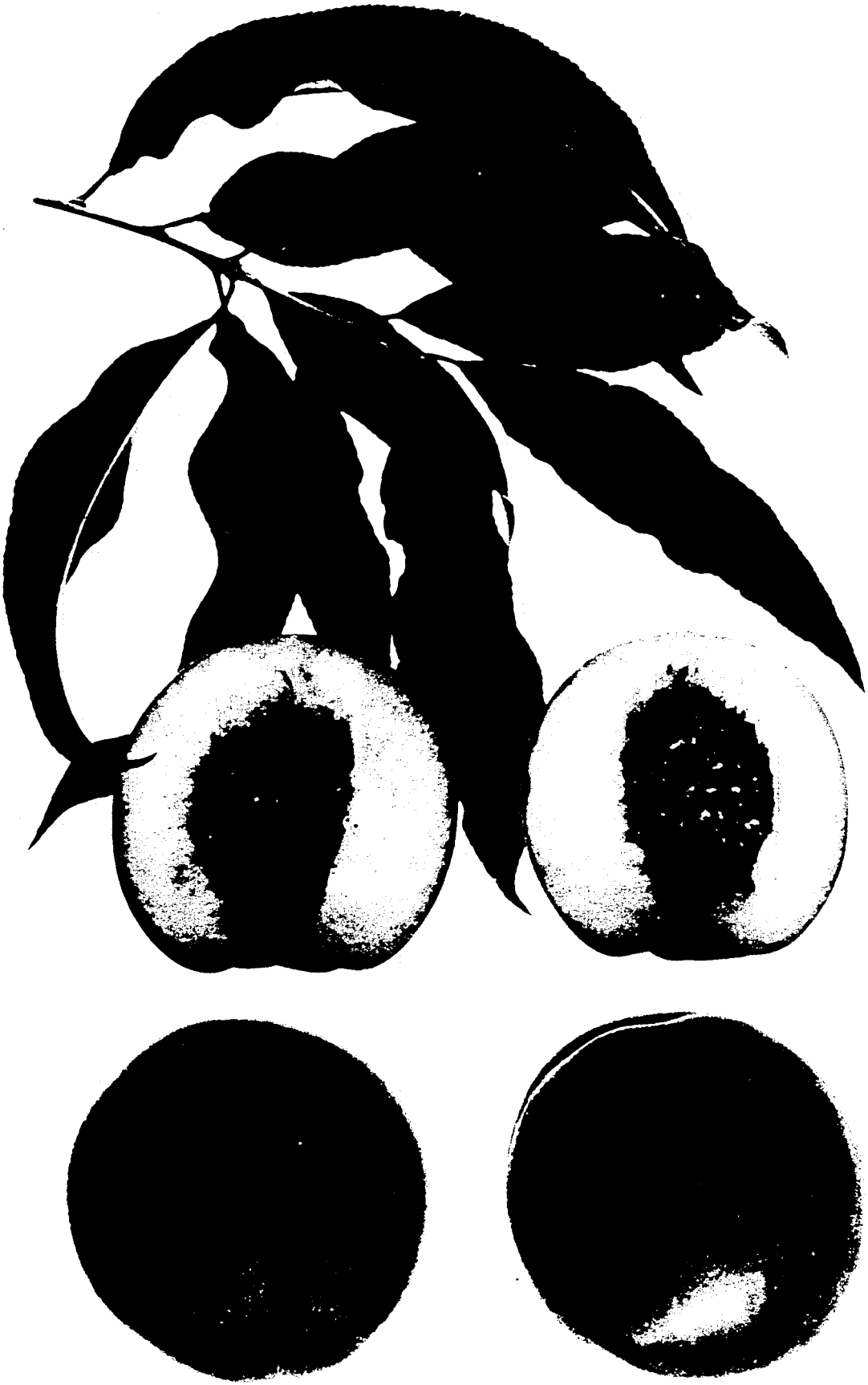

* * * * *